United States Patent [19]

Sinclair

[11] Patent Number: 4,961,872
[45] Date of Patent: Oct. 9, 1990

[54] CALCIUM HYPOCHLORITE TABLETS

[75] Inventor: Richard G. Sinclair, Columbus, Ohio

[73] Assignee: The Drackett Company, Cincinnati, Ohio

[21] Appl. No.: 336,556

[22] Filed: Apr. 7, 1989

Related U.S. Application Data

[60] Division of Ser. No. 117,882, Oct. 26, 1987, abandoned, which is a continuation of Ser. No. 623,268, Jun. 21, 1984, abandoned.

[51] Int. Cl.$^5$ .............. C02F 1/76; A01N 59/00; C01B 11/06
[52] U.S. Cl. .............. 252/186.37; 252/187.24; 252/187.27; 252/187.28; 210/756; 424/661; 424/663
[58] Field of Search .............. 252/186.37, 187.24, 252/187.27, 187.28; 210/756; 424/149; 264/122, 331.15, 331.17, 331.18

[56] References Cited

U.S. PATENT DOCUMENTS

| | | | |
|---|---|---|---|
| 2,921,911 | 1/1960 | Staubly et al. | 252/187.25 |
| 3,036,013 | 5/1962 | Jaszka et al. | 252/99 |
| 3,276,949 | 10/1966 | Robson et al. | 210/764 X |
| 3,647,523 | 3/1972 | Horvath et al. | 252/186.25 X |
| 3,669,894 | 6/1972 | Faust | 252/187.29 |
| 3,793,216 | 2/1974 | Dychdala | 252/186.37 |
| 3,856,932 | 12/1974 | May | 424/16 |
| 3,953,354 | 4/1976 | Faust | 252/186.37 |
| 4,035,484 | 7/1977 | Faust et al. | 424/149 |
| 4,048,351 | 9/1977 | Saeman et al. | 427/213 |
| 4,087,360 | 5/1978 | Faust et al. | 210/701 |
| 4,218,433 | 8/1980 | Kooichi et al. | 424/15 |
| 4,281,421 | 8/1981 | Nyquist et al. | 423/474 X |
| 4,293,426 | 10/1981 | Gago | 427/215 X |
| 4,427,796 | 1/1984 | Nudel et al. | 521/139 |
| 4,865,760 | 9/1989 | Johnson et al. | 252/187.28 |

FOREIGN PATENT DOCUMENTS 332154 1/1970 U.S.S.R. .............. 252/187.28

Primary Examiner—Brooks H. Hunt
Assistant Examiner—Virginia B. Caress
Attorney, Agent, or Firm—Charles J. Zeller

[57] ABSTRACT

A calcium hypochlorite tablet useful as a toilet bowl cleaner, said tablet being prepared by compressing a dry mixture of granular calcium hypochlorite and a finely divided water-insoluble resin having a molecular weight of between about 10,000 to about 1,000,000, which resin is inert to calcium hypochlorite and which has good cold flow characterisitics, said resin comprising from about 10 to about 50% by weight, based on the total weight of the composition.

7 Claims, No Drawings

CALCIUM HYPOCHLORITE TABLETS

This application is a division of Ser. No. 117,882 filed 10/26/87, abandoned which is a continuation of Ser. No. 623,268 filed June 21, 1984, now abandoned.

BACKGROUND OF INVENTION

This invention relates to calcium hypochlorite tablets that are useful as toilet bowl cleaners. More particularly, it concerns tablets of this character that may be employed in single automatic dispensers in toilet bowl tanks. This type of dispenser is characterized as being an aquatic dispenser that is intended to confine the calcium hypochlorite tablet in a space and release small metered doses of chlorine solution at regular intervals.

Calcium hypochlorite tablets conventionally supplied tend to dissolve rapidly on contact with water. This is accompanied by the evolution of large quantities of gas and an enlargement of the tablets. These characteristics are difficult to manage in the aquatic dispensers referred to above.

SUMMARY OF INVENTION

It has now been found that the rate of dissolution of calcium hypochlorite tablets and the enlargement of the volume of these tablets on contact with water (as for example in the aquatic dispensers noted above) can be controlled if said tablets are made by compressing a dry mixture of granular calcium hypochlorite and a sizeable amount of a finely divided water insoluble, high molecular weight resin which is inert to calcium hypochlorite and which has good cold flow characteristics. In a preferred form of this invention, the tablets are also provided with a shell of preformed inert polymer which is open, in a limited fashion, to the surrounding water when the tablet is disposed in the aquatic dispenser.

PRIOR ART

U.S. Pat. No. 4,087,360 to Faust et al discloses the preparation of calcium hypochlorite tablets intended for use in sanitizing the water supply such as in swimming pools. The patentees suggest that their tablets be prepared from mixtures of calcium hypochlorite with low molecular weight polyacrylic acid compounds. The latter are characterized by the patentees as being readily soluble in water. In contrast, the resins employed in the present invention are water insoluble. Although Faust et al broadly suggest that the amount of polyacrylic acid compound that they employ may range from about 0.0001 to 10 percent by weight of the calcium hypochlorite used in the examples they give, this amount never exceeds about 1% by weight. This is far below the quantity of resin utilized in the present tablets.

U.S. Patent 4,035,484, to Faust et al discloses the use of a hydrazide of a monocarboxylic acid in calcium hypochlorite composition for the purpose of controlling the availability of chlorine to bodies of water such as swimming pools. In discussing the prior art, these patentees call attention to the fact that it is known in the prior art to use calcium hypochlorite in mixtures containing, as a binding agent, metal salts of carboxylic acids having at least 10 carbon atoms (German Offenlegungschrift 1,959,708). The use of the synthetic resin employed in the present invention is not disclosed.

The U.S. Patent to Kooichi et al 4,218,433 discloses a constant rate eluting medicinal tablet having at least one hollow depression in the surface of the tablet, the tablet containing a water-soluble active medicament, and, optionally, an inert carrier, said tablet being coated with a water-soluble, water-permeable coating agent. Kooichi et al teaches that the hollow depression provides a site for the elution of the active provided the width thereof is between 0.1 and 1.0 mm and the depth is between 0.1 to 0.4 mm. The coating agent includes methacrylic acid-methacrylic acid ester copolymers and methyl acrylate-methacrylic acid-methyl methacrylate copolymers. The former, in pulverized form, may also be used as the inert carrier.

The Kooichi et al patent is not concerned with the calcium hypochlorite cleaning tablets of the present invention. Furthermore, there is no teaching in Kooichi et al that their methacrylic inert carriers can control the swelling or volume of the tablets, as is characteristic of the present invention. Their teaching is rather that their coating in combination with their depression are the critical elements required to control the rate of elution.

U.S. Pat. No. 3,856,932 to May teaches a tablet containing a solid chlorine releasing compound having a water impervious band circumscribing the tablet side walls. The use of the synthetic resin in the body of the tablet which characterizes the present invention is not shown.

DESCRIPTION OF THE INVENTION

As pointed out above, it is a feature of the present invention to employ as a binder for the calcium hypochlorite, certain organic synthetic resins defined in more detail below. As a group, organic materials would generally be considered unsuitable admixtures for binding together particles of calcium hypochlorite, because of chemical incompatibility. For example, exothermic reactions and fires have resulted from mixing materials such as glycols, polyglycols, and ether structure with calcium hypochloride.

However, in accordance with the present invention, certain organic resins have been found to be effective binders of calcium hypochlorite, without indications of incompatibility. These resins, when finely divided and mixed with granular hypochlorite, assist the formation of strong tablets. Moreover, both the rate of dissolution of calcium hypochlorite and the enlargement of volume are reduced.

To be suitable for use in the present invention, the organic resin selected should have a number of characteristics. An essential characteristic is that it be insoluble in water. It is also necessary that the resin be inert to calcium hypochlorite. It is further important that it show good cold flow properties. Ordinarily, the useful resins will be synthetic in character and will be of high molecular weight, e.g., from about 10,000 to about 1,000,000, preferably from about 50,000 to about 200,000.

A number of resins are known in the prior art which meet these criteria. One class of resins are polymers prepared from chlorinated unsaturated hydrocarbons. These are exemplified by such materials as chlorinated polyethylene, chlorinated polybutadiene, chlorinated polyisoprene, copolymers of ethylene and vinyl chloride and copolymers of vinylidene chloride. The characterisitcs common to these materials are cold flow capability and inertness to calcium hypochlorite.

Another class of resins that is useful for the present purpose are polymers of alkenyl acid esters where the esterifying alcoholic moiety is of sufficient length to promote cold flow and insolubility of hypochlorite within the tablet matrix. A number of resins of this type are available in the prior art. These include such materials as poly n-butyl methacrylate, poly 2-ethylhexyl methacrylate, polypropyl methacrylate, polyisobutyl methacrylate, polyethyl acrylate, polybutyl acrylate, polypropyl acrylate, polyhexyl acrylate, polyhexyl methacrylate, and other acrylic materials, including copolymers of the foregoing, that are not easily oxidized by calcium hypochlorite and that are capable of cold flow when compressed during tabletting.

Especially good results have been obtained with poly n-butyl methacrylates. One such material that is available commercially is Elvacite 2044 from DuPont. This is a homopolymer of n-butyl methacrylate of high molecular weight and having an inherent viscosity of about 0.50 dl./g. (0.25 grams polymer in 50 ml. methylene chloride, measured at 20° C. using a No. 50 Cannon-Fenske viscometer).

The quantity of resin that will be contained in the tablets of the present invention may vary somewhat. What is critical is that a sizeable quantity be present which will give the desired solubility and stability characteristics as well as the cold flow characteristics. Generally the resin will constitute between about 10% and about 50% by weight based on the total weight of the tablet. Preferably, it will be present in the range of from about 15% to about 30% by weight based on the same weight basis.

The bulk of the remaining portion of the tablets of this invention (i.e. over and beyond the resin) will comprise calcium hypochlorite. Other constituents may also be present in this portion of the tablets. Usually, the calcium hypochlorite will constitute from about 50% to about 90% (as is) by weight based on the total weight of the composition. In the preferred aspect of this invention, this will constitute between about 70% to about 85% (as is) by weight on the same weight basis. Typically, commercial calcium hypochlorite has an assay of between about 60 to about 70%, the impurities including, for example, calcium chloride, sodium chloride, calcium chlorate, calcium hydroxide and water.

In addition to the resin and calcium hypochlorite, the tablets of this invention may contain other adjuvants sometimes found in tablets of this character. These include such materials as inert fillers and lubricants utilized in tabletting.

In preparing the tablets of this invention, a dry mix of finely divided resin and granular calcium hypochlorite will first be prepared. The particle size of the resin employed can vary somewhat. Usually, this will be in the range of from about 0.01 to about 1 mm, preferably from about 0.1 to about 0.5 mm. Similarly, the size of the granules of calcium hypochlorite utilized may range over a variety of sizes. For the most part, this particle size will fall within the range of about 0.01 to 0.5 mm, preferably from about 0.05 to about 0.2 mm. The more finely ground the particulate constituents, the more efficient will be the mixing with concomitent reduction in the cold flow requirements of the resin component.

The mix of resin particles and granular calcium hypochlorite will then be pressed in a tabletting machine in accordance with the procedures well known to those skilled in the tabletting art. The specific manner of doing this may vary and does not constitute a part of this invention.

In an alternative form of this invention, the resin bonded calcium hypochlorite tablet described above is emcompassed in a preformed shell of an inert polymer. This shell is fabricated so that it is open, to a limited extent, to permit the water to contact the tablet contained therein. This serves to prolong the integrity of the tablet and controls the admission of water and the release of the desired aqueous solution. It will be recognized that this arrangement provides a monolithic, slow-release device i.e. a controlled-release device that maintains a constant area for dissolution of the bound matrix of active ingredient.

A variety of polymers may be employed in fabricating the preformed shell that will contain the tablet described above. By way of example mention may be made of the following: polyethylene, polypropylene, chlorinated polyethylene, and polymeric esters of methacrylic acid, e.g., Lucite ®. One material that was found to be particularly good for calcium hypochlorite is polyvinyl chloride (PVC).

The following Examples are given to further illustrate the present invention. It is understood, however, that this invention is not limited thereto.

EXAMPLE 1

A mixture of ground poly n-butyl methacrylate (Elvacite 2044, DuPont), 20% by weight, and commercial calcium hypochlorite granules (assay 68.5%), said mixture having an average particle size of about 0.1 mm, was pressed into cylindrical tablets at a pressure of about 2,000 psi. One 40 gram tablet was immersed in 80 milliliters of water, producing a total volume of 102 ml. The total volume was observed periodically for a period of 14 days and found not to exceed 107% of the initial volume. By contrast, a similar experiment with a tablet of unmodified commercial calcium hypochlorite in water experienced a progressive increase in total volume, reaching 154% of the initial volume in a 12-day period.

Subjecting resin-modified tablets to elevated temperatures produced only slight discoloration and no evidence of significant exothermic reaction. Thus, when the resin-modified tablet was heated overnight in a forced draft oven at 165° F., there was no visual change and no exothermic decomposition was observed.

EXAMPLE 2

Tablets were formed within cylindrical lengths of PVC pipe, using (1) unmodified commercial calcium hypochlorite granules and (2) the mixture of Example 1 (with 20% resin). Each pipe section was of 38 mm inside diameter and 20 mm axial length, and each resulting weight (of chemical charge) was approximately 34 grams. As compared to the unmodified hypochlorite tablets, the resin-modified tablets had exposed faces that seemed harder and stronger.

One end of each pipe section was covered with a PVC sheet, cemented in place. The resulting specimens were then placed in beakers of water into which a continuous stream of water was directed. After 18 hours of such activity, the unmodified tablet had disintegrated and dispersed completely, while the resin-modified tablet exhibited only slight erosion of the exposed face.

EXAMPLE 3

Tablets were prepared as in Example 2 but with both ends covered with PVC sheet. Four holes of approximately 1 mm were then pierced into one end face of each specimen, roughly central to equal areas of the face. Plain and resin-modified specimens were placed within water-filled chambers (of toilet cleaning dispensers) that periodically were partially flushed with fresh water. In both specimens, the rate of chlorine release was found to be reduced as compared to that of corresponding hypochlorite tablets not having the monolithic shell, and the rate could be increased by increases of the number (and presumably, the size and position) of the holes in the shell. Only minor enlargement of the volume of solids was evident, as indicated by the slight convexities that appeared in the PVC sheets which formed the ends of the cylindrical shells. However, as between the resin bonded and non-bonded tablets contained in the cylindrical shells, the non-bonded tablet disintegrated within the shell quite rapidly.

What is claimed is:

1. A method of making a calcium hypochlorite tablet comprising the steps of (A) dry mixing from about 50 to about 90% granular calcium hypochlorite and from about 10 to about 50% finely divided water-insoluble resin exhibiting good cold flow characteristics and having a molecular weight from about 10,000 to about 1,000,000, said resin being substantially chemically unreactive with calcium hypochlorite in aqueous media and selected from the group consisting of (a) chlorinated unsaturated hydrocarbons selected from the group consisting of chlorinated polyolefins having five or fewer carbons in the monomeric unit, copolymers of ethylene and vinyl chloride, and copolymers of vinylidene chloride and (b) polyalkenyl acid esters whose esterifying alcoholic moiety contains from 2 to 8 carbon atoms and (B) compressing the dry mix to form a tablet.

2. The method according to claim 1 wherein the polyalkenyl acid esters are selected from the group consisting of polybutyl methacrylate, poly 2-ethylhexyl methacrylate, polypropyl methacrylate, polybutyl acetate, polypropyl acrylate, polyhexyl methacrylate, and polyhexyl acrylate.

3. The method according to claim 1 wherein the chlorinated polyolefin is selected from the group consisting of chlorinated polyethylene, chlorinated polybutadiene and chlorinated polyisoprene.

4. The method according to claim 1 wherein the resin is selected from the group consisting of copolymers of ethylene and vinyl chloride and copolymers of vinylidene chloride.

5. The method according to claim 1 wherein said resin is a poly n-butyl methacrylate.

6. The method according to claim 1 wherein said resin is from about 15 to about 30% by weight and wherein said calcium hypochlorite is from about 70 to about 85% by weight (as is), based on the total weight of said tablet.

7. The method according to claim 6 wherein the resin has a molecular weight of from about 50,000 to about 200,000.

* * * * *